US012766344B2

(12) United States Patent
Yoon

(10) Patent No.: US 12,766,344 B2
(45) Date of Patent: Oct. 20, 2026

(54) OSTEOPOROSIS TREATMENT TOOL, APPARATUS, AND METHOD

(71) Applicant: Young June Yoon, Seoul (KR)

(72) Inventor: Young June Yoon, Seoul (KR)

(*) Notice: Subject to any disclaimer, the term of this patent is extended or adjusted under 35 U.S.C. 154(b) by 50 days.

(21) Appl. No.: 18/904,043

(22) Filed: Oct. 1, 2024

(65) Prior Publication Data

US 2026/0061225 A1 Mar. 5, 2026

(30) Foreign Application Priority Data

Sep. 2, 2024 (KR) ........................ 10-2024-0118368

(51) Int. Cl.
*A61N 7/00* (2006.01)

(52) U.S. Cl.
CPC ........ *A61N 7/00* (2013.01); *A61N 2007/0052* (2013.01)

(58) Field of Classification Search
CPC ........................................................ A61N 7/00
See application file for complete search history.

(56) References Cited

U.S. PATENT DOCUMENTS

| | | | | |
|---|---|---|---|---|
| 2011/0264012 | A1* | 10/2011 | Lautzenhiser | G10K 11/02 601/2 |
| 2018/0214125 | A1* | 8/2018 | Tola | A61B 8/4281 |
| 2022/0152426 | A1* | 5/2022 | Cho | A61N 7/00 |
| 2022/0296214 | A1* | 9/2022 | Zheng | A61B 8/4245 |
| 2022/0331612 | A1* | 10/2022 | Schafer | A61N 7/02 |

FOREIGN PATENT DOCUMENTS

| | | | | |
|---|---|---|---|---|
| CN | 116712685 A | * | 9/2023 | A61N 7/00 |
| KR | 10-2024-0015741 A | | 2/2024 | |

* cited by examiner

*Primary Examiner* — Joanne M Rodden

(57) ABSTRACT

The present disclosure discloses an osteoporosis treatment system, apparatus, and method. According to the present disclosure, the osteoporosis treatment system includes: a solid gel pad that has a groove formed to be inclined in consideration of a main direction of trabeculae for an osteoporosis treatment area of a patient obtained using an imaging device; and a fixing part that fixes the solid gel pad to skins near treatment areas of each patient, wherein a probe of low-intensity pulsed ultrasound is inserted into the groove of the solid gel pad so that pulsed ultrasound applied by the low-intensity pulsed ultrasound amplifies movement of fluid inside a trabecular bone to maximize a response of osteoblasts distributed on a surface of the trabeculae.

6 Claims, 6 Drawing Sheets

- Prior Art -

OSTEOPOROSIS TREATMENT TOOL, APPARATUS, AND METHOD

CROSS-REFERENCE TO RELATED APPLICATION

This application claims the benefit of priority under 35 U.S.C. § 119 (a) to Korean Patent Application No. 10-2024-0118368 filed on Sep. 2, 2024, the entire contents of which are incorporated herein by reference.

BACKGROUND

(a) Technical Field

The present disclosure relates to an osteoporosis treatment system, apparatus, and method.

(b) Background Art

According to Medical News Today, approximately 5% of population in the United States suffers from osteoporosis in a femoral head.

The femoral head refers to a head portion of a femur, which is a thigh bone.

One of the fields of ultrasound currently being studied, low-intensity pulsed ultrasound (LIPUS), has stimulated that stem cells in osteoporosis in the femoral head play a role in differentiating into osteoblasts.

This means that the osteoporosis may be treated therapeutically using the LIPUS method.

FIG. 1 is a diagram illustrating osteoblasts, which are distributed on a surface of trabeculae within the femoral head, and osteoblasts are differentiated and reacted according to the flow of fluid inside the trabecular bone.

Accordingly, when the fluid flow inside the trabecular bone stimulates the osteoblasts, responding to the mechanical stimulus, such as the fluid flow.

SUMMARY OF THE DISCLOSURE

In order to solve the problems of the above-described related art, the present disclosure is to provide an osteoporosis treatment system, apparatus, and method capable of maximizing the relative movement of fluid to osteoblasts.

In order to achieve the above object, according to an aspect of the present disclosure, an osteoporosis treatment system includes: a solid gel pad that has a groove formed to be inclined in consideration of a main direction of trabeculae as osteoporotic patients are treated by ultrasound using imaging device; and a fixing part that fixes the solid gel pad to skins near treatment areas of each patient, in which a probe of low-intensity pulsed ultrasound is inserted into the groove of the solid gel pad so that pulsed ultrasound applied by the low-intensity pulsed ultrasound amplifies movement of fluid inside a trabecular bone to maximize a response of osteoblasts distributed on a surface of the trabeculae.

An inclination angle of the groove may vary depending on the main direction of the trabeculae of each patient.

The solid gel pad having the groove formed to be inclined in the main direction of the trabeculae of each patient may be manufactured using methods that use cutting, mold, die, or 3D printing.

The solid gel pad may include: a probe insertion part that is formed at an upper portion; a groove that is formed to be inclined from the probe insertion part in consideration of the main direction of the trabeculae; and a solid gel that surrounds the groove and serves as a moving medium of the pulsed ultrasound.

The imaging device may be at least one of an X-ray device, computed microscopy (CT), magnetic resonance imaging (MRI), and dual-energy X-ray absorptiometry (DEXA).

The inclination angle of the groove may be determined in consideration of a diffraction phenomenon due to a difference between the main direction of the trabeculae and the direction of the wave velocity of the pulsed ultrasound between a bone cortex and a soft tissue.

According to another aspect of the present disclosure, an osteoporosis treatment apparatus includes: a storage unit that stores information on a main direction of trabeculae for an osteoporosis treatment area of a patient obtained using an imaging device; and a pad generation unit that manufactures a solid gel pad having a groove formed to be inclined in consideration of a main direction of trabeculae corresponding to patients using the information on the main direction, wherein the solid gel pad is disposed on a skin near a treatment area of the patients, and a probe of low-intensity pulsed ultrasound is inserted into the groove so that pulsed ultrasound applied by the low-intensity pulsed ultrasound amplifies movement of fluid inside a trabecular bone to maximize a response of osteoblasts distributed on a surface of the trabeculae.

According to still another aspect of the present disclosure, an osteoporosis treatment method includes the steps of: exploring a main direction of trabeculae for an osteoporosis treatment area of a patient using an imaging device; manufacturing a solid gel pad having a groove formed to be inclined in consideration of the explored main direction; disposing the solid gel pad on a skin near a treatment area of a patient; inserting a probe of low-intensity pulsed ultrasound into the groove; and applying pulsed ultrasound to the treatment area through the probe, wherein the pulsed ultrasound amplifies movement of fluid inside a trabecular bone to maximize a response of osteoblasts distributed on a surface of the trabeculae.

According to the present disclosure, by applying the pulsed ultrasound while considering the main direction of the trabeculae of each patient, it is possible to maximize the effect of the osteoporosis treatment.

DETAILED DESCRIPTION

Figure 1:
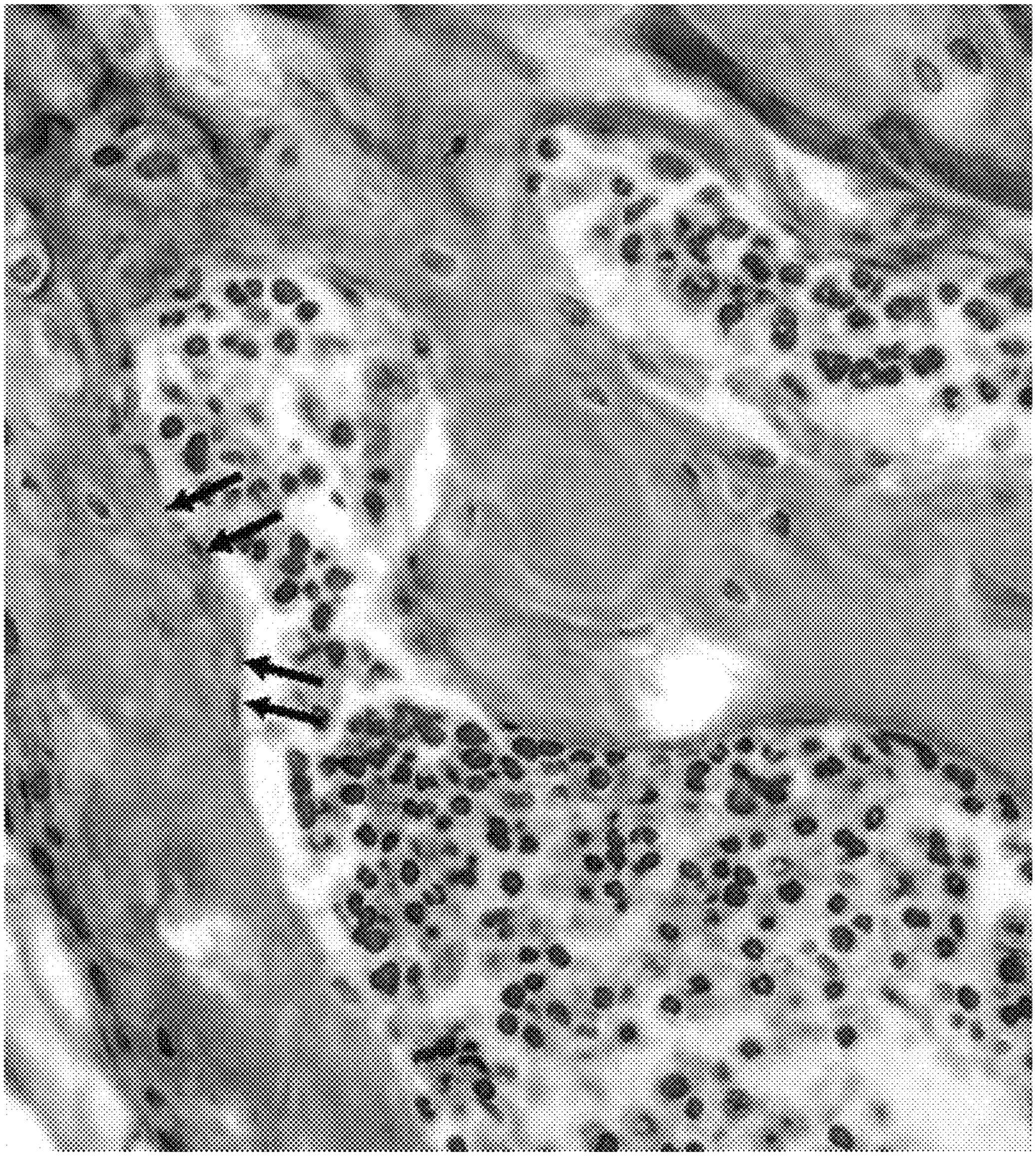
FIG. 1 is a diagram illustrating osteoblasts.

Since the present disclosure may be variously modified and have several exemplary embodiments, specific exemplary embodiments will be illustrated in the accompanying drawings and be described in detail. However, it is to be understood that the present disclosure is not limited to a specific embodiment, but includes all modifications, equivalents, and substitutions without departing from the scope and spirit of the present disclosure.

The terms used in the present specification are used only to describe specific embodiments rather than limiting the present disclosure. Singular forms include plural forms unless the context clearly indicates otherwise. It should be understood that the term "include" or "have" used in the present specification is intended to specify the presence of features, numerals, steps, operations, components, parts described in the present specification, or combinations thereof, but is not intended to preclude the presence or addition of one or more other features, numerals, steps, operations, components, parts, or combinations thereof.

In addition, components of the embodiments described with reference to each drawing are not limitedly applied only to the corresponding embodiment, and may be implemented to be included in other embodiments within the scope of maintaining the technical spirit of the present disclosure. In addition, it goes without saying that these components may also be re-implemented as one embodiment in which a plurality of embodiments are integrated, even if a separate description is omitted.

In addition, in the description with reference to the accompanying drawings, regardless of reference numerals, the same components will be given the same or related reference numerals and duplicate description thereof will be omitted.

Figure 2:
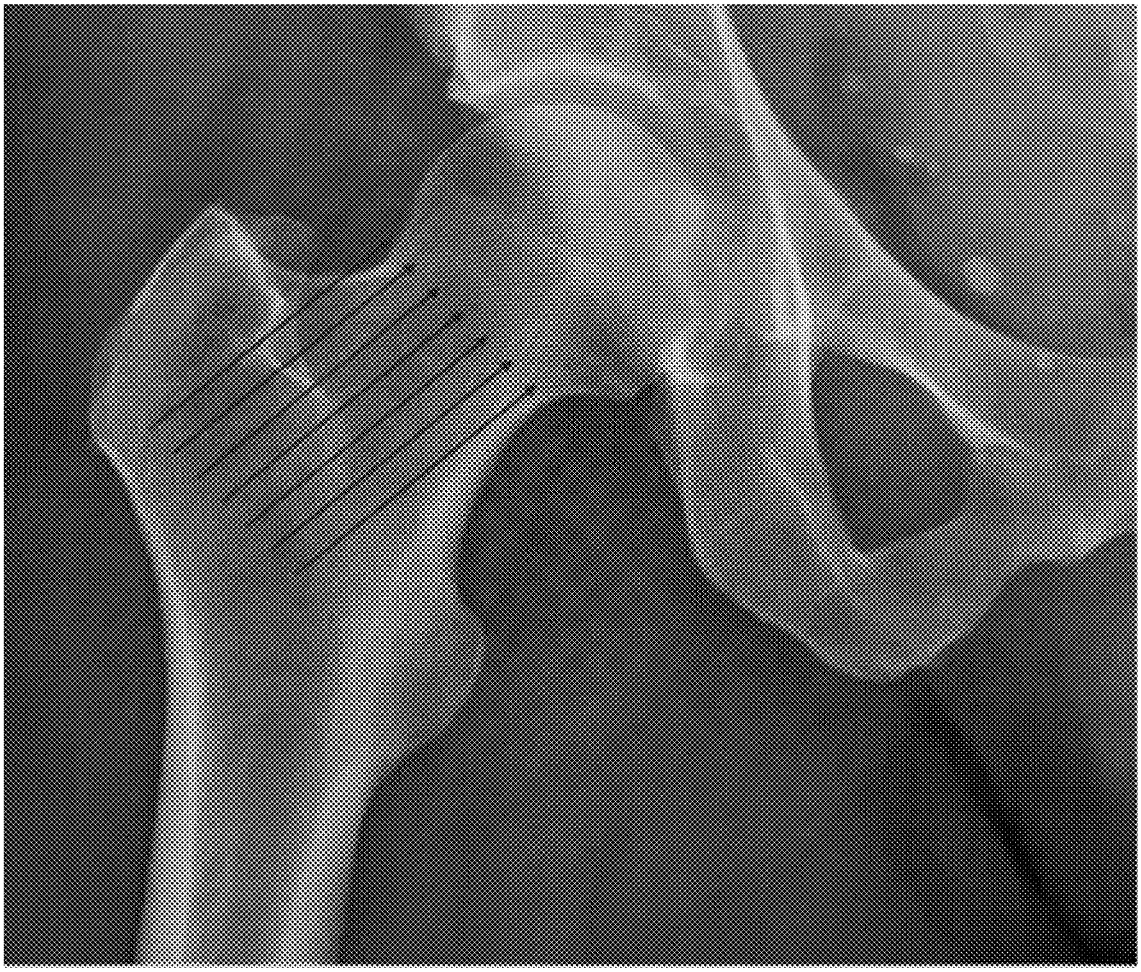
FIG. 2 is a diagram illustrating an X-ray image of a femoral head.

FIG. 2 is a diagram illustrating an X-ray image of a femoral head.

In FIG. 2, a main direction of trabeculae inside a tissue is indicated by a direction of an arrow.

Trabeculae are small beams, struts, or rod-shaped microscopic tissue elements that support or fix a skeleton of a tissue, and directionality of the trabeculae varies uniquely from a patient to another patient.

In the present embodiment, a method of maximizing an effect of LIPUS in a simple manner in consideration of a main direction of trabeculae is proposed.

Figure 3:
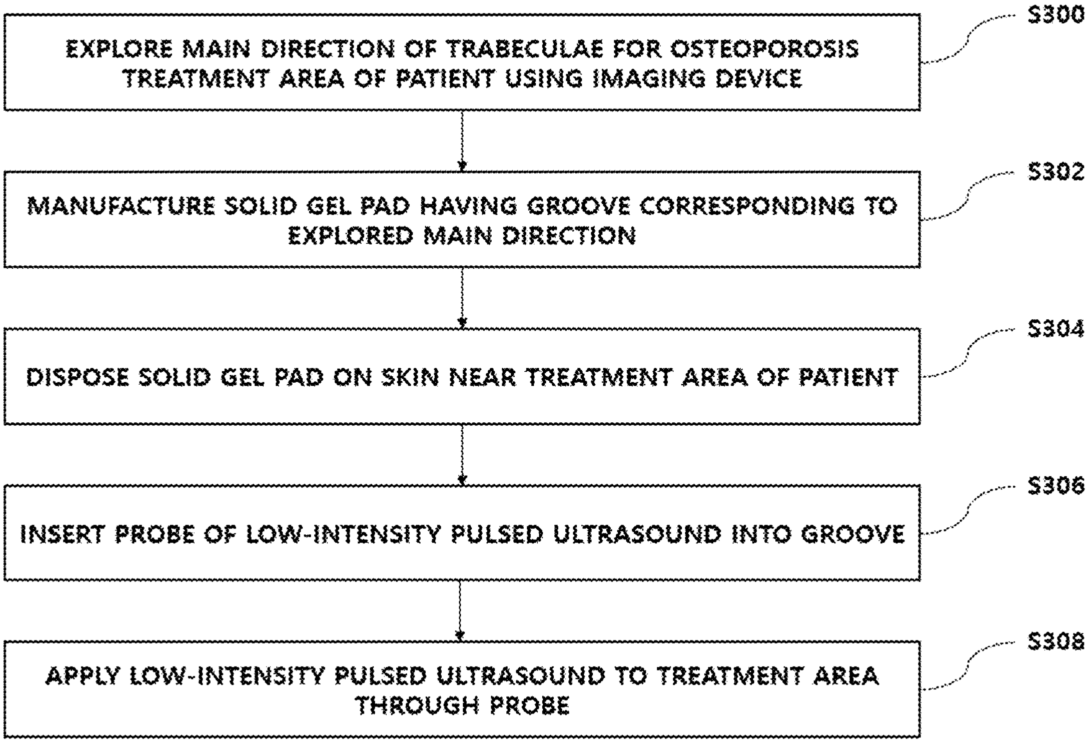
FIG. 3 is a flowchart illustrating a process of maximizing an LIPUS effect according to an embodiment of the present disclosure.

FIG. 3 is a flowchart illustrating a process of maximizing an LIPUS effect according to an embodiment of the present disclosure.

Referring to FIG. 3, a main direction of trabeculae for an osteoporosis treatment area of a patient is explored using an imaging device (step 300).

Here, an imaging device may be various imaging devices such as an X-ray device, computed microscopy (CT), magnetic resonance imaging (MRI), and dual-energy X-ray absorptiometry (DEXA).

Next, a solid gel pad having a groove corresponding to the explored main direction of trabeculae is manufactured (step 302).

In general, low-intensity pulsed ultrasound uses a liquid gel as a moving medium for ultrasound, but in the present embodiment, the solid gel pad is provided so that the pulsed ultrasound may be applied considering the main direction of the trabeculae explored for each patient, and the groove corresponding to the explored main direction is formed in the solid gel pad.

Figure 4:
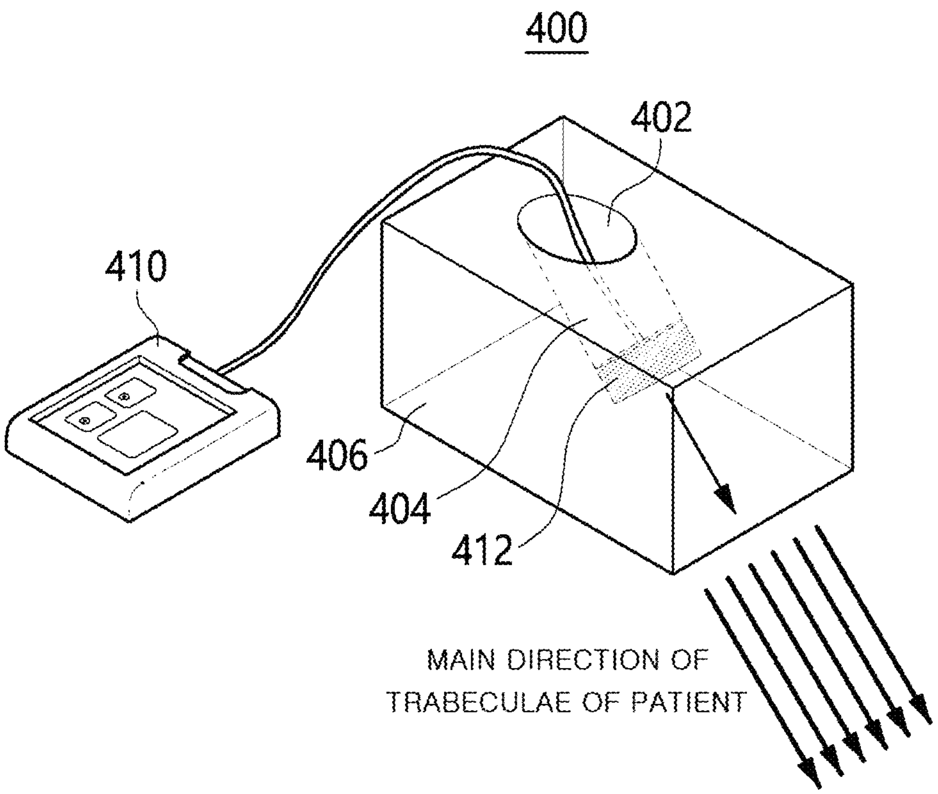
FIG. 4 is a diagram illustrating a detailed configuration of a solid gel pad according to an embodiment of the present disclosure.

As illustrated in FIG. 4, a solid gel pad 400 according to an embodiment of the present disclosure may include a probe insertion part 402 into which a probe 412 of low-intensity pulsed ultrasound 410 is inserted, a groove 404 that is formed to be inclined from the probe insertion part 402 toward a main direction of trabeculae, and a solid gel 406 that surrounds the groove 404 and serves as a moving medium for pulsed ultrasound.

The solid gel pad 400 may have various shapes. In the present embodiment, the solid gel pad 400 is illustrated as a hexahedral shape, but is not necessarily limited thereto, and is disposed on a skin near a treatment area of a patient so that a direction of the groove 404 is parallel to the main direction of the trabeculae.

The solid gel pad according to the present embodiment may use methods including cutting processing, mold, die, and 3D printing to form the groove 404 inclined corresponding to the main direction of the trabeculae obtained for each patient.

The solid gel pad may be manufactured using cutting processing, a mold molding method, a die molding method, 3D printing, etc., using information on the main direction of the trabeculae of each patient, and the information on the patient may be stored in a connected storage unit, and the solid gel pad may be manufactured to correspond to a main direction of trabeculae of a specific patient according to a request of a worker.

Figure 5:
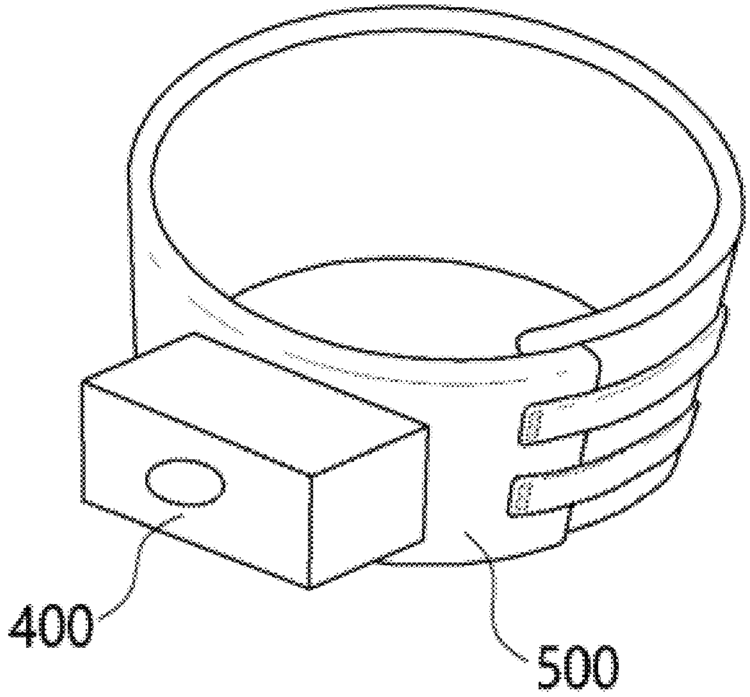
FIG. 5 is a diagram illustrating a structure for connecting a fixing part to the solid gel pad according to an embodiment of the present disclosure.

When treating osteoporosis of a patient, as illustrated in FIG. 5, the solid gel pad 400 is disposed on the skin near the treatment area of the patient using a fixing part 500 (step 304), and the probe 412 of the low-intensity pulsed ultrasound is inserted into the groove 404 (step 306).

The fixing part 500 has the solid gel pad 400 attached to the end, and is provided in a Velcro®-type band shape so that the solid gel pad 400 may be disposed on a treatment area of a patient.

Generally, the probe has a circular or rectangular shape, but may have a different shape depending on the manufacturer. The groove 404 formed on the solid gel pad 400 may also be manufactured to fit the shape of the probe.

After the probe 412 is disposed inside the groove 404, the low-intensity pulsed ultrasound is applied to the treatment area of the patient through the probe 412 (step 308).

According to an embodiment of the present disclosure, the treatment effect may be maximized by inserting the probe 412 of the low-intensity pulsed ultrasound into the groove 404 of the solid gel pad 400.

When the main direction of the trabeculae and the direction of the low-intensity ultrasound application inside the bone corresponding to the treatment area are aligned, the movement of fluid adjacent to osteoblasts may be amplified to maximize the response of the osteoblasts, thereby enhancing the osteoporosis treatment effect.

Hereinafter, the theoretical approach according to the present embodiment will be described in detail.

An equation of poroelastic theory regarding a poroelastic material may be expressed in two equations as follows.

Here, the poroelastic material is a material having multiple pores and through which fluid can flow in the pores.

The equation of poroelastic theory for measuring a flow velocity is as follows.

$$\rho_{11}\ddot{u} + \rho_{12}\ddot{U} - Nu_{i,jj} - (A+N)u_{j,ji} + b(\dot{u}_i - \dot{U}_i) = 0 \quad \text{[Equation 1]}$$

$$\rho_{22}\ddot{U}_i + \rho_{12}\ddot{u}_i - (RU_{j,j} + Qu_{j,j}) - b(\dot{u}_i - \dot{U}_i) = 0 \quad \text{[Equation 2]}$$

Here, P, R, and Q are poroelastic modulus, and N is later merged into P=A+2N and expressed as P. The poroelastic modulus is defined separately below. u and U are displacements of solid and fluid parts, which represent the displacements of the fluid and trabeculae inside the trabecular bone. Differentiating the displacements once with respect to time represents velocity.

The constant b is expressed as $\phi^2\mu/kp$, where μ represents the viscosity of the fluid, kp represents the permeability of the fluid. ϕ represents porosity. For the relative ratio of the displacement of the fluid and the displacement of the trabeculae, the following Ui=r·ui is defined.

Here, r represents a relative ratio, and u and U have periodicity and are expressed as wavenumber (k) and frequency (ω). Equations 1 and 2 are expressed as follows.

$$(Pk^2-(\omega^2\rho_{11}+i\omega b))+r(Qk^2-(\omega^2\rho_{12}-i\omega b))=0 \quad \text{[Equation 3]}$$

$$r(Qk^2-(\omega^2\rho_{12}-i\omega b))+r^2(Rk^2-(\omega^2\rho_{22}-i\omega b))=0 \quad \text{[Equation 4]}$$

Since the second term of Equation 3 and the first term of Equation 4 are the same, the relative ratio may be found as follows.

$$r^2=\frac{1}{De}(\mathrm{Re}+i\,\mathrm{Im}), \quad \text{[Equation 5]}$$

$$\mathrm{Re}=(Rk^2-\omega^2\rho_{22})\cdot(Pk^2-\omega^2\rho_{11})+(\omega b)^2,$$

$$\mathrm{Im}=\omega b[(Rk^2-\omega^2\rho_{22})-(Pk^2-\omega^2\rho_{11})],$$

$$De=[(Pk^2-\omega^2\rho_{11})^2+(\omega b)^2].$$

Here, the poroelastic modulus P, Q, and R are defined as follows:

$$P=\frac{\phi(K_s/K_f-1)K_b+\phi^2K_s+(1-2\phi)(K_s-K_b)}{(1-\phi-K_b/K_s+\phi K_s/K_f)}+\frac{4G}{3} \quad \text{[Equation 6]}$$

$$Q=\frac{(1-\phi-K_b/K_s)\phi K_s}{1-\phi-K_b/K_s+\phi K_s/K_f} \quad \text{[Equation 7]}$$

$$R=\frac{K_s\phi^2}{(1-\phi-K_b/K_s+\phi K_s/K_f)} \quad \text{[Equation 8]}$$

$k_b$ represents bulk modulus when the inside of the trabecular bone is empty, $k_s$ represents bulk modulus of the trabecula, $k_f$ represents bulk modulus of the fluid existing inside the trabecular bone, and G is shear modulus of the trabecula.

The physical properties used in the calculation are as follows.

The Young's modulus (GPa) of the trabecular bone including the porosity is $E_b=1.89\cdot10^{10}\cdot(1-\phi)^{1.95}$.

The Poisson's ratio of the trabecular bone including the porosity is $v=0.198\cdot(1-\varphi)^{-0.16}$.

The shear modulus (GPa) of the trabecular bone including the porosity is $G=7.94\cdot10^{9}\cdot(1-\phi)^{1.99}$.

The Young's modulus of the trabeculae is $E_s$=18 GPa.

The relational equation of density defined in the poroelastic theory is as follows. The subscripts 11, 12, and 22 of the density are newly defined density definitions in the poroelastic theory, and for the subscripts s and f, s represents the density corresponding to the trabecular or solid part, and f represents the density corresponding to the fluid part occupying the empty space or the interstitial fluid part.

$$\rho_{11}+\rho_{12}=(1-\phi)\rho_s,$$

$$\rho_{22}+\rho_{12}=\phi\rho_f,$$

$$\rho_{12}=(1-t)\phi\rho_f.$$

$$b=10^{-9},$$

$$\phi=0.7,$$

$$\rho_s=1960\frac{\mathrm{kg}}{\mathrm{m}^3},$$

$$\rho_f=1000\frac{\mathrm{kg}}{\mathrm{m}^3},$$

$$K_f=2.3\ \mathrm{GPa}$$

The Poisson's ratio of the trabeculae is $v_s$=0.302.

Figure 6:
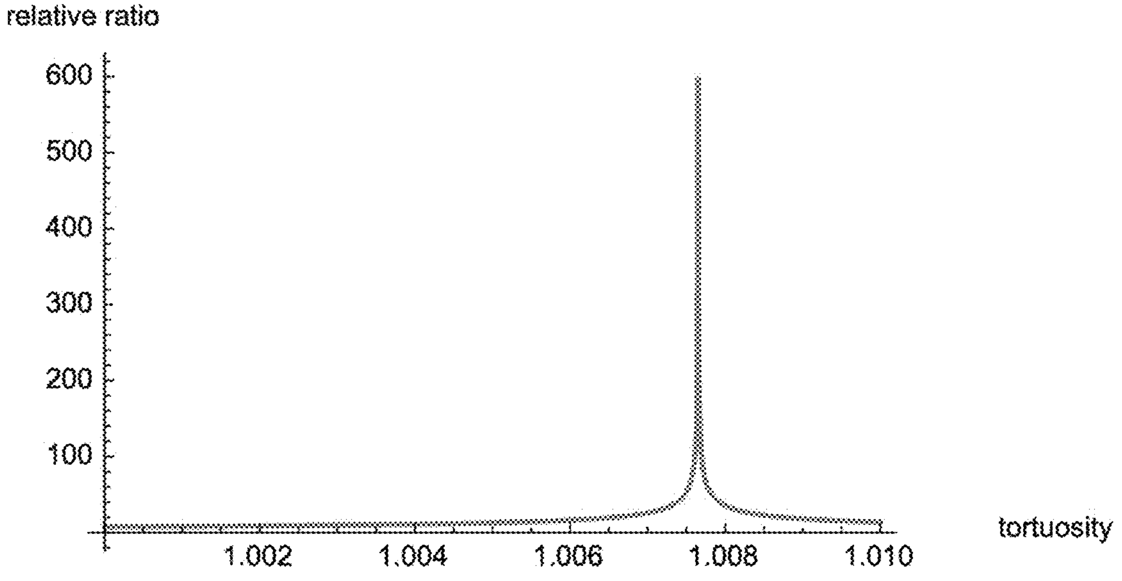
FIG. 6 is a diagram illustrating the LIPUS effect according to an embodiment of the present disclosure.

FIG. 6 is a diagram illustrating the LIPUS effect according to an embodiment of the present disclosure.

$$\left(t=\frac{C}{L},\right.$$

Referring to FIG. 6, referring to tortuosity wherein C represents the actual length and L represents a straight-line distance between two points. When it is a straight line, tortuosity t becomes 1) and the relative movement of the fluid, when there was about 7.7% difference in tortuosity, it was confirmed that the relative movement of the fluid to solid bone matrix was maximized when the wave goes through the direction of trabecula.

Therefore, it can be seen that the apparatus according to the present embodiment maximizes the effect when the ultrasound waveform is transmitted along the main direction of the trabeculae.

When the pulsed ultrasound passes through the solid gel pad and passes through the skin or soft tissue, the diffraction due to the change between the soft tissue and the solid gel is not expected to change significantly because the mechanical properties are similar. However, when the wave enters the bone cortex (the outer part of the bone) from the soft tissue, the diffraction occurs due to the difference in physical properties, so the angle needs to be adjusted.

The Snell's law as shown in the following Equation may be referenced.

$$\frac{\sin\theta_1}{\sin\theta_2}=\frac{v_1}{v_2} \quad \text{[Equation 9]}$$

The speed of the bone cortex is known to be 3250 m/s, and the speed of the soft tissue is known to be 1430 to 1647 m/s. Assuming that the main component of the solid gel pad attached to the skin surface is similar to the physical properties of water, whose speed of the pulsed ultrasound is 1481 m/s. The maximum speed of soft tissue is 1647 m/s, and the average value between the water wave velocity and the soft tissue wave velocity is considered as the wave velocity of soft tissue. It is assumed that there is no diffraction between the soft tissue and the solid gel.

According to the present embodiment, in order to correct the diffraction value due to the diffraction phenomenon caused by the difference between the speed of the bone cortex and the speed of soft tissue, the inclination of the groove 404 inside the solid gel pad 400 is determined so that the direction of propagation of the ultrasound waveform propagating in the bone cortex matches the direction of the trabeculae.

The embodiments of the present disclosure described above have been disclosed for illustrative purposes, and those skilled in the art with ordinary knowledge of the present disclosure will be able to make various modifications, changes, and additions within the spirit and scope of the present disclosure, and these modifications, changes, and additions should be regarded as falling within the scope of the following claims.

What is claimed is:

1. An osteoporosis treatment system, comprising: a solid gel pad configured to be disposed on skin adjacent to an osteoporosis treatment area of a patient, the solid gel pad including a groove having an inclination angle, the groove being structurally formed in the solid gel pad such that, when the solid gel pad is positioned on the skin, the groove is oriented along a main direction of trabeculae of the osteoporosis treatment area, wherein the main direction is identified from image data obtained by an imaging device; and a fixing structure physically connected to the solid gel pad and configured to mechanically secure the solid gel pad to the skin of the patient, wherein the groove is dimensioned and shaped to receive a probe for low-intensity pulsed ultrasound such that, upon insertion of the probe into the groove, pulsed ultrasound is configured to emit from the probe and configured to propagate through the solid gel pad along the inclination angle of the groove and into the osteoporosis treatment area, thereby amplifying relative movement of fluid within a trabecular bone so as to increase a response of osteoblasts distributed on a surface of the trabeculae.

2. The osteoporosis treatment system of claim 1, wherein the inclination angle of the groove is selected based on the identified main direction of the trabeculae of the patient such that the inclination angle of the groove is patient-specific.

3. The osteoporosis treatment system of claim 1, wherein the groove having the inclination angle is formed during manufacture of the solid gel pad by at least one of cutting, molding, die forming, or three-dimensional printing.

4. The osteoporosis treatment system of claim 1, wherein the solid gel pad further includes: a probe insertion portion is formed at an upper portion of the solid gel pads; and a solid gel material surrounding the groove and configured to provide an ultrasound transmission medium between the probe and the skin.

5. The osteoporosis treatment system of claim 1, wherein the image data is used to determine the main direction of the trabeculae prior to placement of the solid gel pad.

6. The osteoporosis treatment system of claim 1, wherein the inclination angle of the groove is configured to compensate for refraction of an ultrasound wave occurring at an interface between soft tissue and a bone cortex, such that a propagation direction of the ultrasound wave inside the bone cortex is substantially coincident with the main direction of the trabeculae.

* * * * *